(12) United States Patent
Yamaya et al.

(10) Patent No.: US 9,029,787 B2
(45) Date of Patent: May 12, 2015

(54) MULTI-PURPOSE PET DEVICE

(75) Inventors: Taiga Yamaya, Chiba (JP); Hideo Murayama, Chiba (JP)

(73) Assignee: National Institute of Radiological Sciences, Chiba (JP)

(*) Notice: Subject to any disclaimer, the term of this patent is extended or adjusted under 35 U.S.C. 154(b) by 642 days.

(21) Appl. No.: 13/255,769

(22) PCT Filed: Mar. 12, 2009

(86) PCT No.: PCT/JP2009/054781
§ 371 (c)(1),
(2), (4) Date: Feb. 29, 2012

(87) PCT Pub. No.: WO2010/103645
PCT Pub. Date: Sep. 16, 2010

(65) Prior Publication Data
US 2012/0161014 A1    Jun. 28, 2012

(51) Int. Cl.
*G01T 1/164* (2006.01)
*G01T 1/29* (2006.01)
*G01T 1/16* (2006.01)

(52) U.S. Cl.
CPC .............. *G01T 1/2985* (2013.01); *G01T 1/1603* (2013.01)

(58) Field of Classification Search
CPC .................................................. G01T 1/2985
USPC ............. 250/363.02, 363.03, 363.04, 363.05; 382/131
See application file for complete search history.

(56) References Cited

U.S. PATENT DOCUMENTS

| 5,444,252 A * | 8/1995 | Hug et al. ................. 250/363.08 |
| 6,490,476 B1 * | 12/2002 | Townsend et al. ............ 600/427 |
| 6,831,961 B1 * | 12/2004 | Tybinkowski et al. ............ 378/4 |
| 7,180,074 B1 * | 2/2007 | Crosetto ................. 250/370.09 |
| 2003/0076925 A1 | 4/2003 | DeSilets et al. |
| 2003/0118155 A1 | 6/2003 | Ueno et al. |
| 2003/0128801 A1 * | 7/2003 | Eisenberg et al. .............. 378/19 |
| 2003/0179853 A1 * | 9/2003 | Amemiya et al. .............. 378/63 |
| 2004/0022350 A1 * | 2/2004 | Gregerson et al. .............. 378/15 |
| 2004/0097800 A1 * | 5/2004 | Crosetto ....................... 600/407 |
| 2005/0109943 A1 * | 5/2005 | Vaquero et al. .......... 250/363.04 |

(Continued)

FOREIGN PATENT DOCUMENTS

| JP | A-2001-159682 | 6/2001 |
| JP | A-2003-190135 | 7/2003 |

(Continued)

OTHER PUBLICATIONS

Iida et al., A New PET Camera for Noninvasive Quantitation of Physiological Functional Parametric images, "Quantification of Brain Function Using PET," Chapter 12, 1996, pp. 57-61, Academic Press, Inc.
International Search Report in International Application No. PCT/JP2009/054781; dated Jun. 16, 2009 (with English-language translation).

*Primary Examiner* — David Porta
*Assistant Examiner* — Djura Malevic
(74) *Attorney, Agent, or Firm* — Oliff PLC

(57) ABSTRACT

In an open PET device including a plurality of detector rings that are arranged apart in the direction of the body axis of a subject and having a physical open field of view area, at least one of the detector rings or another imaging device arranged in parallel is configured to be movable by simple device moving means in order to change the configuration of the PET device. This improves the versatility of the open PET device for easier introduction to facilities.

12 Claims, 19 Drawing Sheets

(a) CONVENTIONAL PET MODE    (b) OpenPET MODE

(56) References Cited

U.S. PATENT DOCUMENTS

| | | | |
|---|---|---|---|
| 2006/0120511 A1* | 6/2006 | Gregerson et al. | 378/198 |
| 2007/0080295 A1* | 4/2007 | Hamill | 250/363.03 |
| 2008/0025460 A1* | 1/2008 | Li | 378/15 |
| 2009/0195249 A1* | 8/2009 | DeMeester et al. | 324/318 |
| 2009/0226066 A1* | 9/2009 | Williams et al. | 382/131 |
| 2010/0183213 A1* | 7/2010 | Keppel et al. | 382/131 |
| 2011/0288407 A1* | 11/2011 | Brinks et al. | 600/427 |

FOREIGN PATENT DOCUMENTS

| | | |
|---|---|---|
| JP | A-2005-505376 | 2/2005 |
| JP | A-2008-134205 | 6/2008 |
| JP | A-2008-307083 | 12/2008 |
| WO | WO 2008/129666 A1 | 10/2008 |

* cited by examiner

Fig. 1
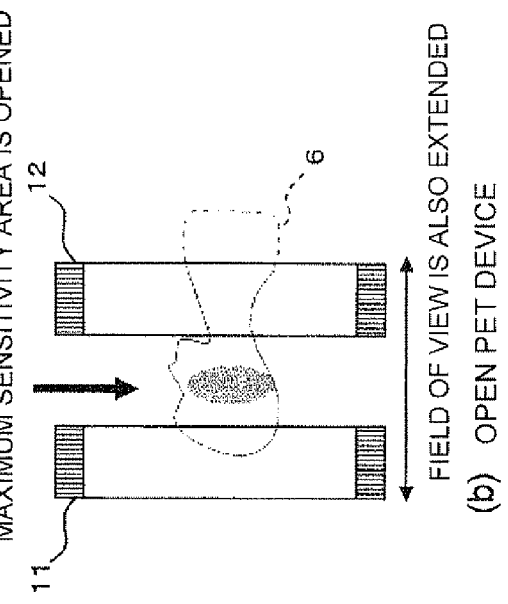
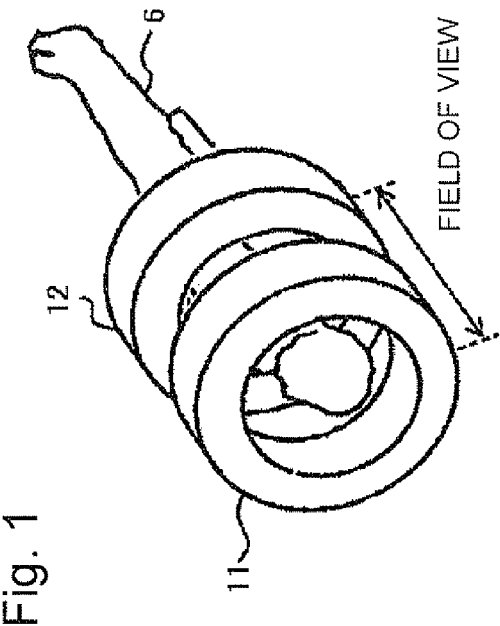
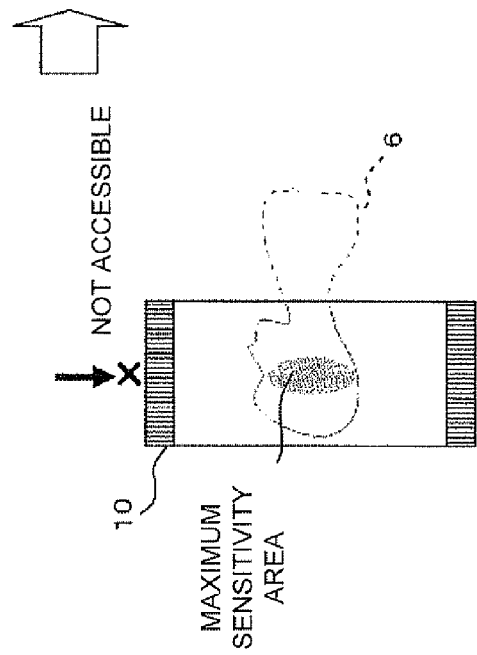
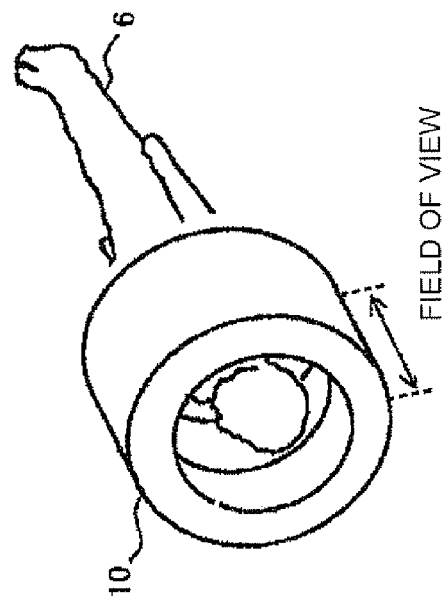
(a) CONVENTIONAL PET DEVICE
(b) OPEN PET DEVICE (a) CONVENTIONAL PET MODE    (b) OpenPET MODE (a) CONVENTIONAL PET MODE    (b) OpenPET MODE

MULTI-PURPOSE PET DEVICE

TECHNICAL FIELD

The present invention relates to an open PET device that includes a plurality of separate detector rings arranged apart in the direction of the body axis of a subject and has a physically open field of view area, and more particularly to a multi-purpose PET device that can be easily changed in configuration.

BACKGROUND ART

Positron emission tomography (PET) is attracting attention as an effective inspection method for earlier diagnosis of cancer, cerebrovascular disease, dementia, etc. In PET, a compound labeled with a trace amount of positron emitting nuclides is administered and annihilation radiation emitted from inside the body is detected to image metabolic functions such as sugar metabolism and check for a disease and its extent. PET devices for practicing PET have been put into actual use.

To improve the sensitivity of a PET device, as illustrated in FIG. 1(a), a detector 10 needs to be arranged in a tunnel-like configuration for an increased solid angle. The long tunnel-shaped patient port, however, increases psychological stress on a patient 6 under examination as well as obstructs the patient's treatment. In view of this, the applicant has proposed an open PET device (also referred to as OpenPET) as illustrated in FIG. 1(b). In the open PET device a plurality of separate detector detectors 11 and 12 are arranged apart in the direction of the body axis to provide a physically open field of view area (also referred to as an open field of view) (WO 2008/129666 publication).

An open PET device enables PET diagnosis during treatment and whole-body simultaneous scanning, which have not been possible with conventional PET devices. Application to real-time PET/CT is also possible. Specifically, treatment can be applied to an open field of view between the detector rings. In an example of radiation cancer therapy, as shown in FIG. 2(a), it is possible to check the position of the cancer by using the open PET device during irradiation with a radiation treatment beam, or visualize the irradiation field of a radiation treatment beam with the open PET device in real time. Since an open PET device can extend the field of view in the direction of the body axis as much as the open field of view without increasing detectors, it is possible to build a PET device that can scan the whole body at a time (also referred to as a whole-body simultaneous field of view PET device) as shown in FIG. 2(b). In the diagram, 11 to 14 designate four detector rings, for example. PET devices capable of whole-body simultaneous scanning are expected to be useful even for the promotion of microdose tests which are attracting attention as a method for improving the development efficiency of drugs. The application of an open PET device to a PET/CT device which has become prevalent recently can easily provide the configuration that an X-ray CT device 20 is disposed in an open space interposed between two detector rings as shown in FIG. 2(c). It is therefore possible to build a real-time PET/CT device for simultaneous diagnosis of the same location, which has not been possible with conventional PET/CT devices. While the example has dealt with a CT device, any imaging devices may be installed in the open space.

As has been described above, an open PET device is expected to be the core of various use forms such as a whole-body simultaneous field of view PET device and a real-time PET/CT device. It may be difficult, however, to install various devices at a time since respective PET devices are expensive. Considering a wide variety of use forms of PET, including cancer screening, ordinary facilities such as a hospital do not always need an open PET device for all inspections from the early stage. Facility planning then needs to take account of up to final use forms, and devices need to be gradually added after initial installation of minimum necessary equipment. The devices need also be planned so that the added devices interact effectively to minimize the idle time of the respective devices.

It is therefore desired that device configurations can be changed depending on the type of inspection, whereas complicated changes in device configuration are unfavorable because PET devices and CT devices are heavy in weight and susceptible to vibrations etc.

DISCLOSURE OF THE INVENTION

The present invention has been achieved in order to solve the foregoing conventional problems. It is thus an object of the present invention to improve the versatility of an open PET apparatus for easier introduction to facilities.

Specifically, the present invention is directed to allowing changes in the configuration of an open PET device by simple device moving means so that a plurality of single PET devices and a single open PET device can be switched easily. In PET inspections where the open field of view is not needed, the detector rings of the open PET device can be used as respective single PET devices to perform a plurality of PET inspections at the same time. This can increase the use efficiency of the PET facility. This also allows gradual introduction of the open PET device into facilities.

FIG. 4 shows the concept of an extendable PET device. As shown in FIG. 4(a), a conventional PET device (also referred to as a first PET device) including only one detector ring 31 (also referred to as a first detector ring) is initially introduced. Then, another PET device (also referred to as a second PET device) including only a second detector ring 41 is added so that the two detector rings 31 and 41 can be used as a single open PET device as shown in FIG. 4(b). The detector ring(s) of at least one of the PET devices (in the diagram, the detector ring 41 of the second PET device) can be placed on rails or otherwise configured so as to be movable in the direction of the body axis of the patient 6, the subject. This makes it possible to freely change the open field of view in size. In inspections where the open field of view is not needed, the two detector rings may be put close to each other to eliminate the open field of view as shown to the right in FIG. 4(b). This allows use as a single high-sensitivity PET device that is long in the direction of the body axis. In the diagram, 32 designates a patient bed, 33 designates a base of the patient bed 32, and 44 designates the rails for the linear movement of the detector ring 41.

It should be appreciated that FIG. 4(a) shows the configuration in which the detector ring 31 of the first PET device is fixed to the floor and the patient bed 32 can be moved for whole-body inspection. However, the detector ring 31 of the first PET device may be configured to be movable while the patient bed 32 is fixed. The detector ring 31 of the first PET device and the patient bed 32 both may be configured to be movable.

FIG. 5 shows a configuration that allows switching between (a) a conventional PET mode in which the first and second detector rings 31 and 41 for constituting an open PET device are used as two independent conventional PET devices to perform two PET inspections in parallel and (b) an Open-PET mode in which the first and second detector rings 31 and 41 are combined and used as a single open PET device. In a) the conventional PET mode, patient beds 32 and 42 held by bases 33 and 43 both are configured to be movable in the direction of the body axis so as to allow whole-body PET inspections. The second detector ring 41 is configured to be movable on rails 44' that extend in a direction orthogonal to the body axis. A single open PET device using both the detector rings 31 and 41 can be configured by withdrawing the patient bed 42 from the patient port of the detector ring 41, moving the patient bed 32 temporarily to the right in the diagram, and then moving the second detector ring 41 to a position coaxial with the first detector ring 31 and returning the patient bed 32 to the original position as shown in FIG. 5(b). The first detector ring 31 itself may be fixed to the floor. To change the size of the open field of view more freely, it is preferred that the first detector ring 31 be configured to be movable on rails 34 in the direction of the body axis.

The movement of two PET devices has been implemented in an apparatus that can locate two PET devices over the head and chest for the purpose of simultaneous PET measurement of brain and heart regions. (H. Iida, et al., "A New PET Camera for noninvasive quantitation of physiological functional parametric images. HEADTOME-V-Dual.," Quantification of brain function using PET (eds. R. Myers, V. Cunningham, D. Bailey, T. Jones) p. 57-61, Academic Press, London, 1996) Such an apparatus, however, is intended to perform coincidence measurements with the two PET devices independently, where no concept or technique is involved to detect and image radiations from nuclides lying in the open space area.

The present invention also allows switching between three or more single PET devices and a single open PET device. FIG. 6 shows how configuration is switched from three single PET devices shown in FIG. 6(a) to a single open PET device shown in FIG. 6(b). In the diagram, 51 designates a third detector ring, 52 designates a patient bed thereof, and 54' designates rails thereof. For example, the detector rings 31 and 41 may constitute an open PET device while the detector ring 51 is used as a single PET device. In FIG. 6, the bases of the patient beds are not shown.

The present invention has been achieved in view of the foregoing findings, and provides a multi-purpose PET device being an open PET device including a plurality of detector rings that are arranged apart from each other in a direction of a body axis of a subject, a physical open field of view area being formed between the rings, the PET device including device moving means for moving the detector rings or device moving means for moving another device into the open space in order to change a configuration of the PET device, the moving of the moving means being in a linear direction or in a direction including a linear direction and a rotating direction.

Here, the moving means may move at least one of the detector rings in the direction of the body axis so as to constitute a single PET device having a plurality of detector rings connected together.

The moving means may move at least one of the detector rings to constitute a plurality of independent PET devices.

The moving may be in a direction orthogonal to the body axis.

The moving may be in the direction of the body axis.

Another imaging device may be arranged in parallel with the PET device, and the device moving means may be means for moving at least one of the detector rings and the imaging device.

The detector rings of the PET device may be movable to positions to interpose the imaging device therebetween from both sides so that a field of view of the imaging device is included in the open field of view area of the PET device.

At least one of the detector rings of the PET device may be movable close to another imaging apparatus so as to allow use as a plurality of independent hybrid imaging devices.

The detector rings of the PET device with which the another imaging apparatus is arranged in parallel may be rotatable.

The another imaging device may be an X-ray CT device.

According to the present invention, it is possible to improve the versatility of an open PET apparatus for easier introduction to facilities. Specifically, since the configuration of the open PET device can be changed by simple device moving means, it becomes possible to easily switch between a plurality of single PET devices and a single open PET device. In PET inspections where the open field of view is not needed, the PET device can be used as single PET devices to perform a plurality of PET inspections at the same time. This can increase the use efficiency of the PET facility. This also allows gradual introduction of the open PET device into facilities.

BRIEF DESCRIPTION OF THE DRAWINGS

FIG. 1 is a diagram showing the basic configuration of a conventional PET device and an open PET device;

BEST MODE FOR CARRYING OUT THE INVENTION

Hereinafter, embodiments of the present invention will be described in detail with reference to the drawings.

Figure 7:
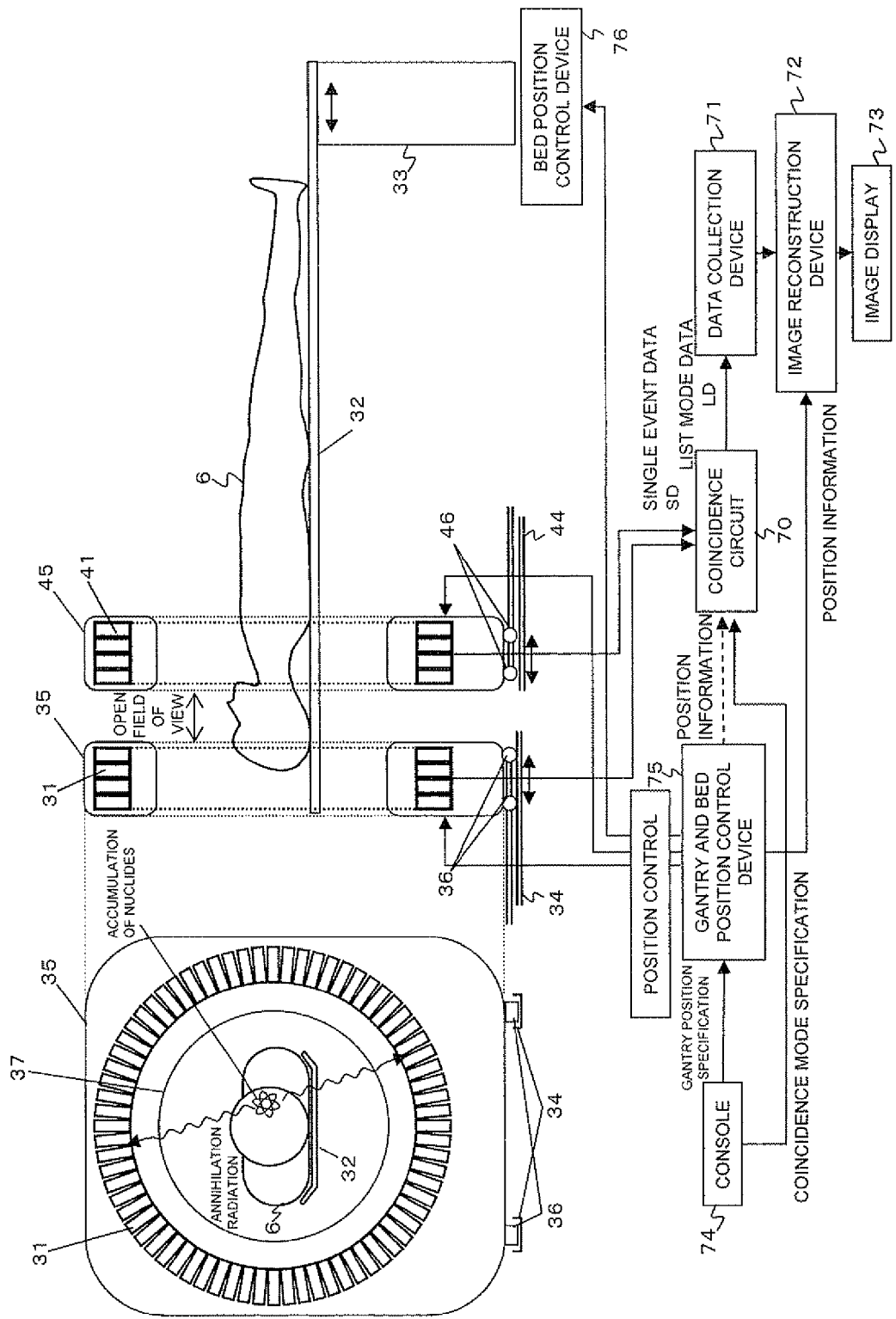
FIG. 7 is a diagram showing a first embodiment of the present invention.

FIG. 7 shows the configuration of an open PET device, a first embodiment of the present invention, which includes two single PET devices. The open PET device includes detector rings 31 and 41, gantry covers 35 and 45 which cover the respective detector rings, and a bed 32 on which a patient 6 lies. The gantries 35 and 45 are equipped with wheels 36 and 46, and have the function of moving back and forth on rails 34 and 44, respectively. In the diagram, 37 designates a patient port.

Nuclides accumulated in the body of the patient 6 emit a pair of annihilation radiations which travel at angles of approximately 180° from each other in all directions. Single event data SD, which is the measured data on either one of a pair of annihilation radiations, detected by the detector rings 31 and 41 is transmitted to a common coincidence circuit 70. The single event data SD is converted into list mode data LD which is information on a coincidence pair. The list mode data LD is stored into a recording medium by a data collection device 71 before transmitted to an image reconstruction device 72 for image reconstruction operation. The reconstructed image is then displayed by an image display 73. The movement of the detector rings 31 and 41 and the patient bed 32 is controlled by a gantry and bed position control device 75 based on gantry and bed position information which is specified from a console 74. The gantry position information and the bed position information are either included into the list mode data LD through the coincidence circuit 70 or directly transmitted to the image reconstruction device 72 so that the calculation for an image reconstruction operation can be performed based on the actual position information on the detectors. In the diagram, 76 designates a bed position control device.

Either a conventional PET mode or an OpenPET mode is selected from the console 74. The mode is transmitted to the coincidence circuit 70 as coincidence mode specification information.

In FIG. 7, there are three possible patterns of coincidence, including within the detector ring 31, within the detector ring 41, and between the detector rings 31 and 41. Possible coincidence pairs in the conventional PET mode are either within the detector ring 31 or within the detector ring 41 (in the case of two inspections in parallel, within the respective detector rings 31 and 41). The three patterns of coincidence may be constantly acquired so that needed data can be selected from the list mode data LD after the completion of the measurement. The coincidence counting between the detector rings 31 and 41, however, is unnecessary in the case of the conventional PET mode.

Figure 8:
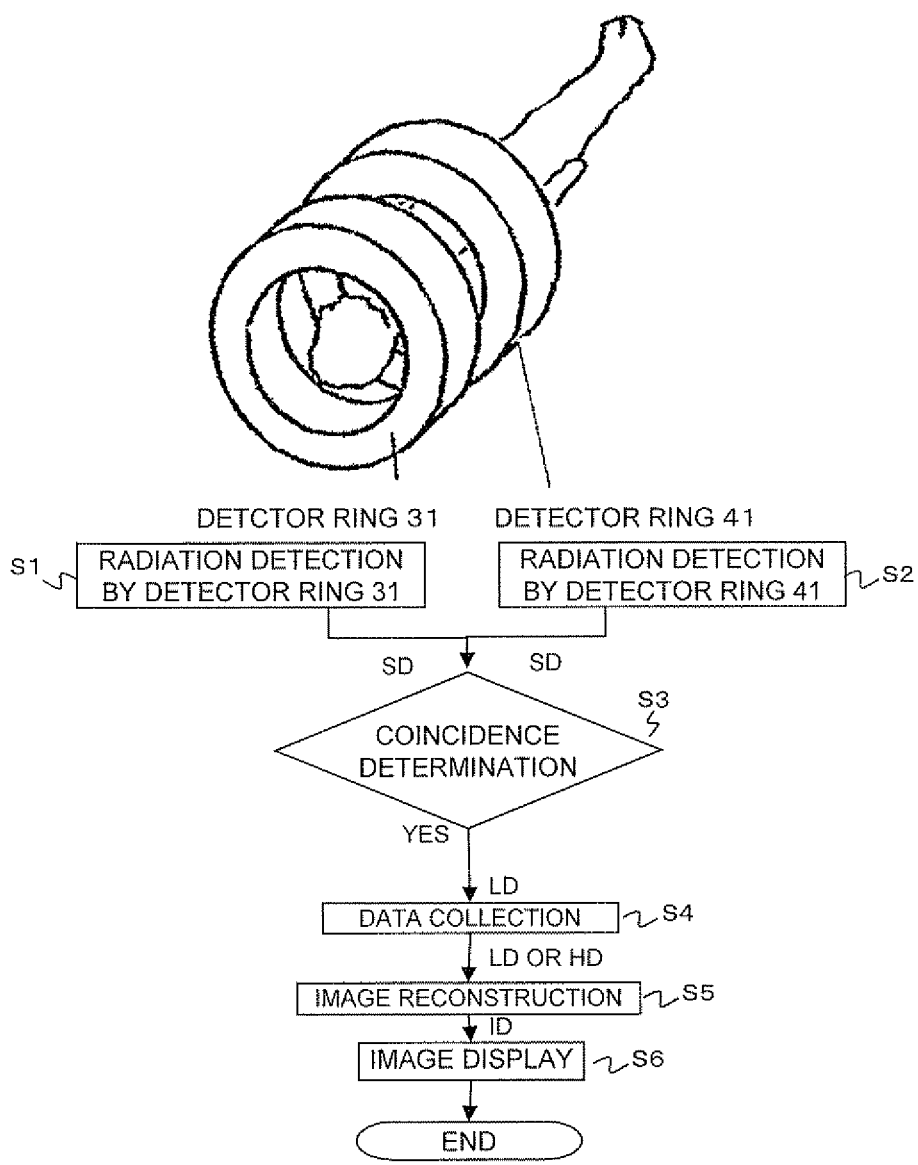
FIG. 8 is a diagram showing an example of operation of the first embodiment.

FIG. 8 shows a procedure when a coincidence determination is made only on necessary pairs based on the coincidence mode specification information in order to reduce the load of the data collection system. When a radiation is detected by the detector ring 31 or 41 (step S1 or S2), position information on the detection element that detects the radiation, energy information on the radiation, and detected time information are taken out as single event data SD. Such single event data SD is transmitted to the coincidence circuit 70 in succession, and a coincidence determination is made on coincidence pairs listed in Table 1 (marked with a circle in the chart) (step S3). The result is converted into list mode data LD which is the information on a pair of detection elements that have detected a pair of annihilation radiations. The data collection device 71 either simply stores the list mode data LD into a storage device or stores the list mode data LD into a storage device as histogram data HD (step 54). The image reconstruction device 72 then performs image reconstruction calculations (step 55) to acquire image data ID which is a tomographic image, and displays the image data ID on the image display 73 (step 56).

TABLE 1

| | | Coincidence pair | | |
|---|---|---|---|---|
| Mode | Remarks | Within first detector ring 31 | Within second detector ring 41 | Between detector rings 31 and 41 |
| Conventional PET mode | First PET device | ○ | | |
| | Second PET device | | ○ | |
| Open PET mode | Entire field of view | ○ | ○ | ○ |
| | Open field of view alone | | | ○ |

○: Coincidence pair

Figure 9:
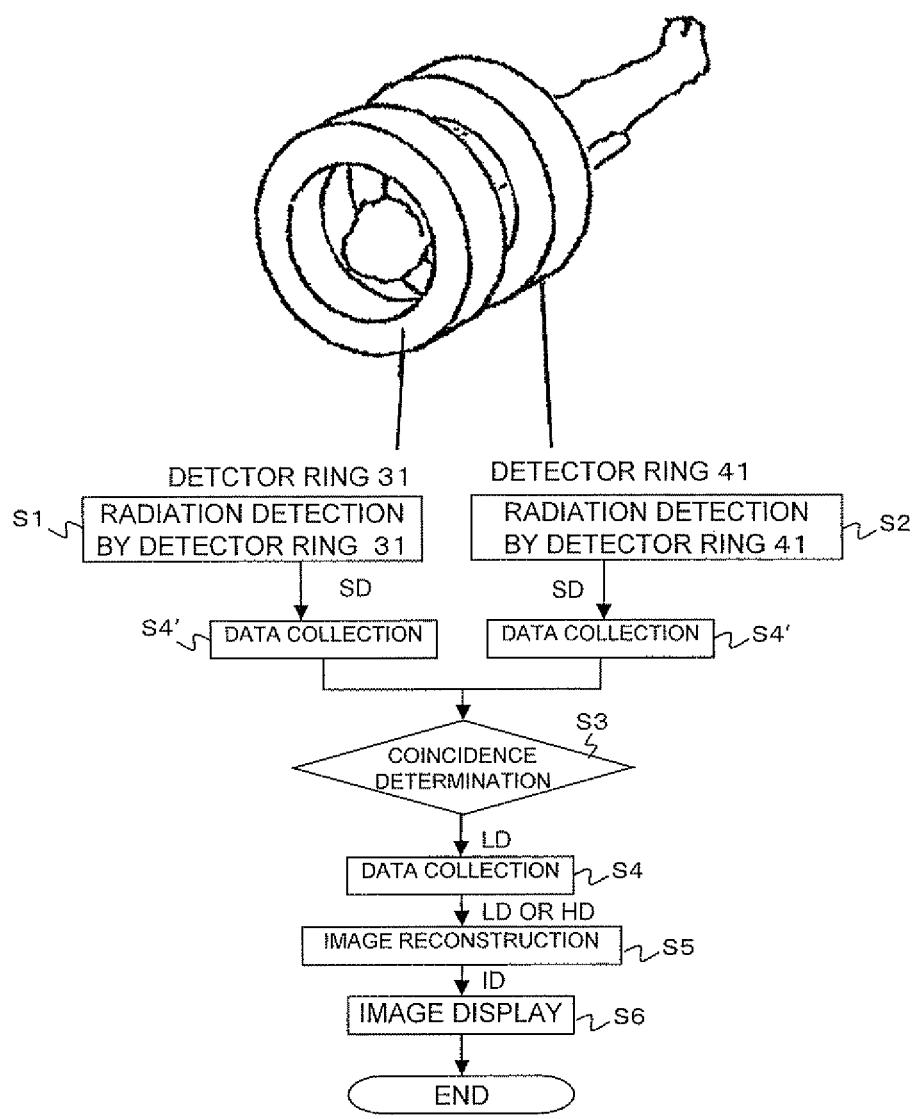
FIG. 9 is a diagram showing another example of the operation of the first embodiment.

FIG. 9 shows the procedure that implements the coincidence determination of FIG. 8 by software means. Single event data SD measured by each of the detector rings 31 and 41 is directly stored into a storage device (step S4'), and then converted into list mode data LD according to coincidence pair control shown in Table 1. A coincidence determination may be made after a series of PET measurements is completed, or in parallel with PET measurements. While FIG. 9 shows the procedure of collecting single event data SD from each of the detector rings 31 and 41 independently, single event data SD from both detector rings may be stored into a common storage device.

Figure 10:
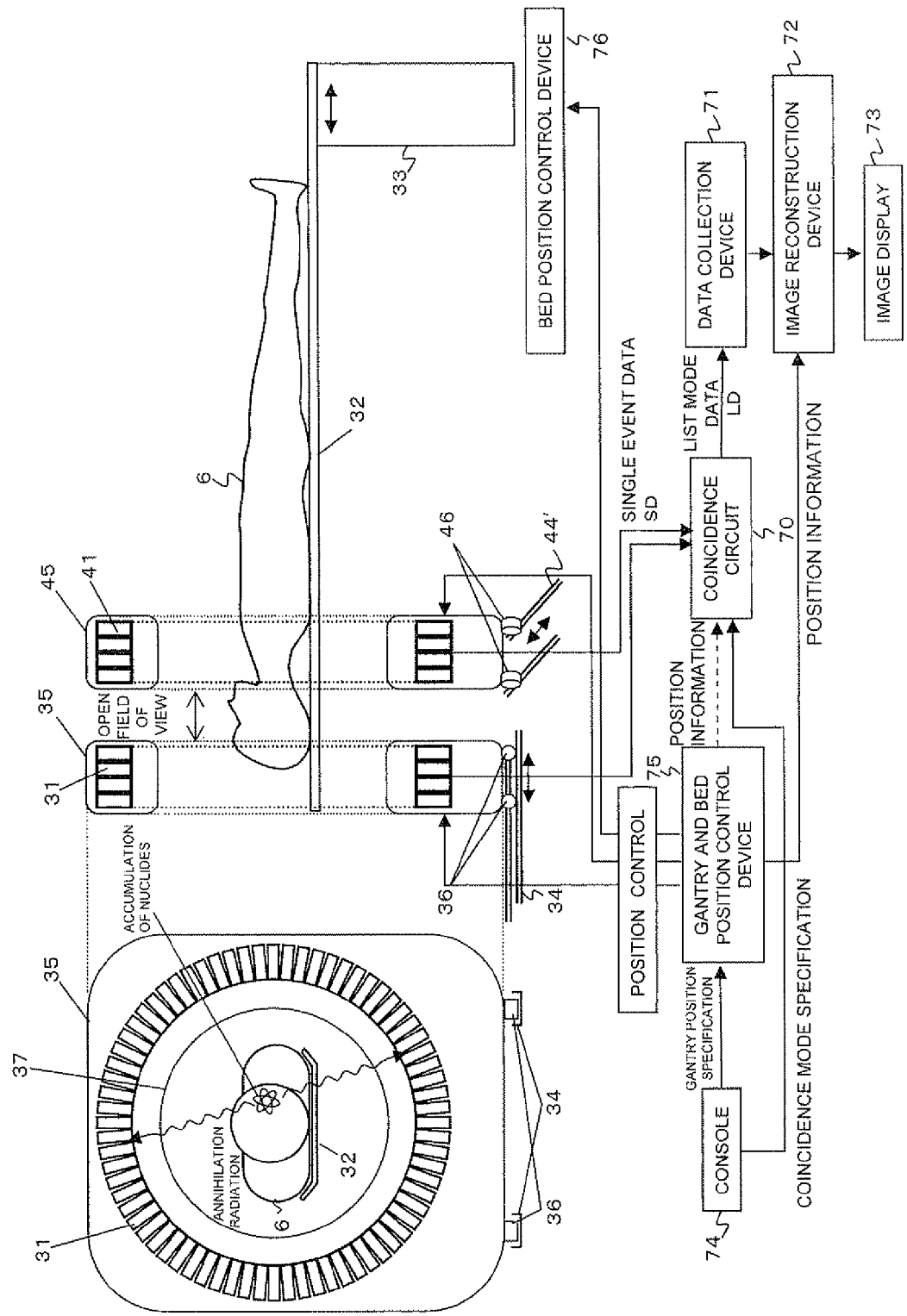
FIG. 10 is a diagram showing a second embodiment of the present invention.

FIG. 10 shows a second embodiment of the present invention. The present embodiment differs from the first embodiment in that the second detector ring 41 is configured to be movable on rails 44' in a direction orthogonal to the direction of the body axis. In other respects, the present embodiment is the same as the first embodiment. A description thereof will thus be omitted.

Figure 2:
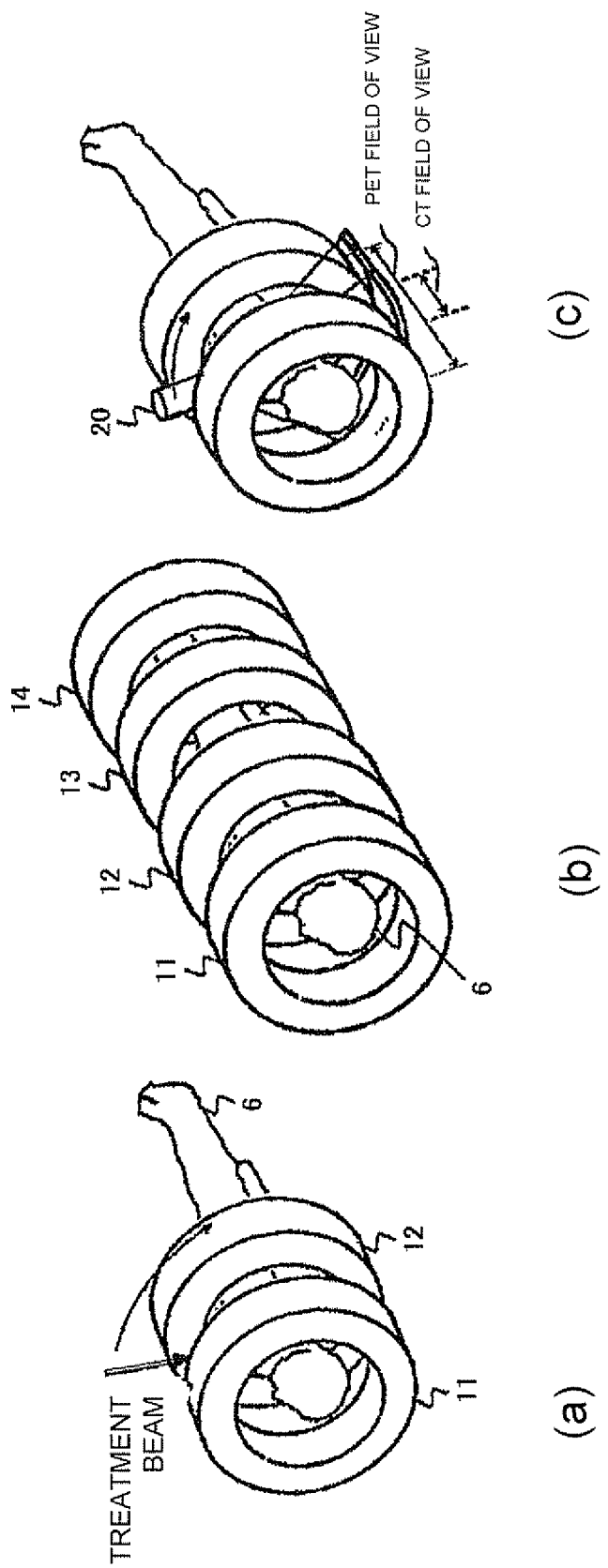
FIG. 2 is a diagram showing application examples of an open PET device.
Figure 3:
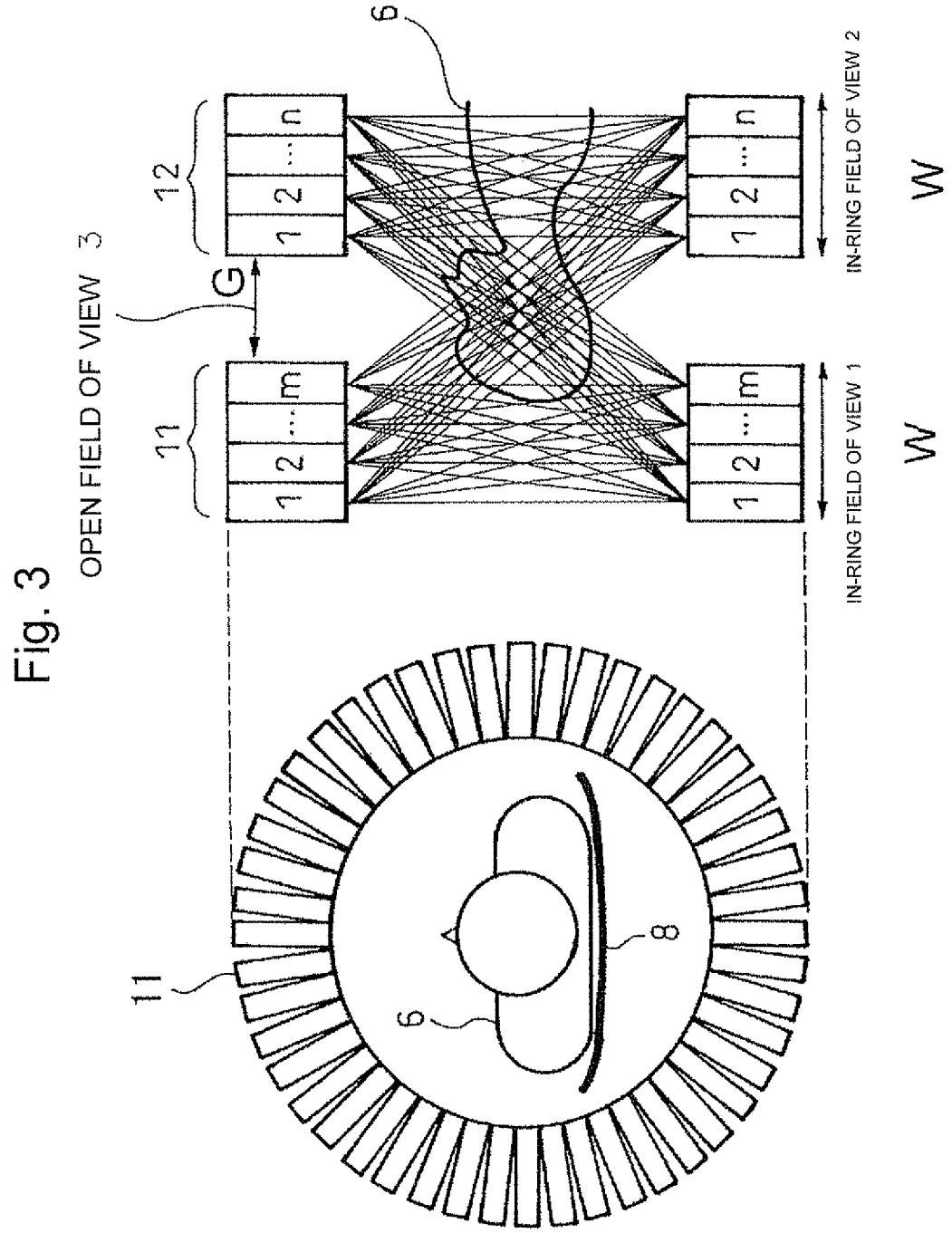
FIG. 3 is a diagram showing the principle of an open PET device.
Figure 4:
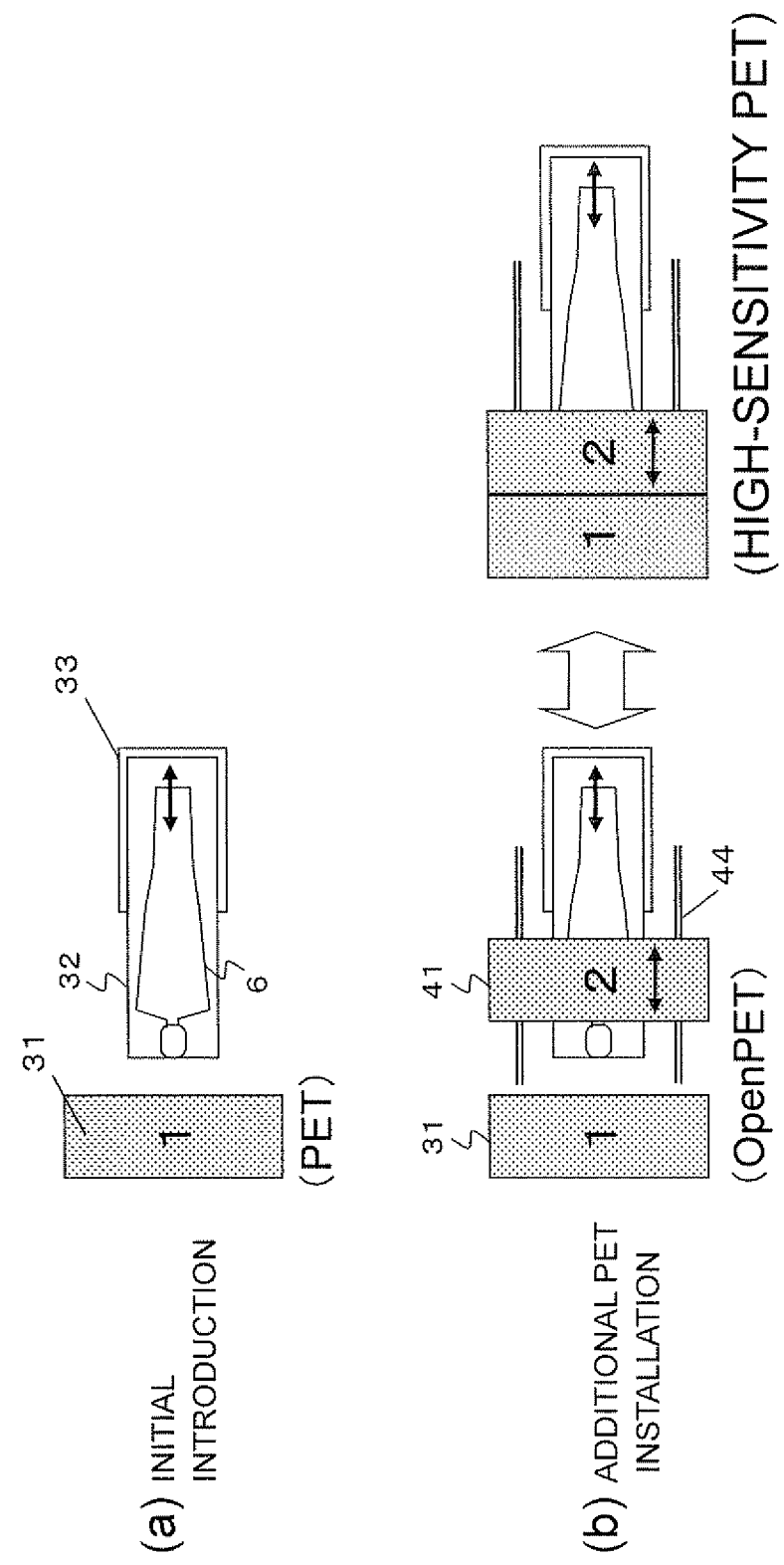
FIG. 4 is a diagram showing a configuration example of the present invention.
Figure 5:
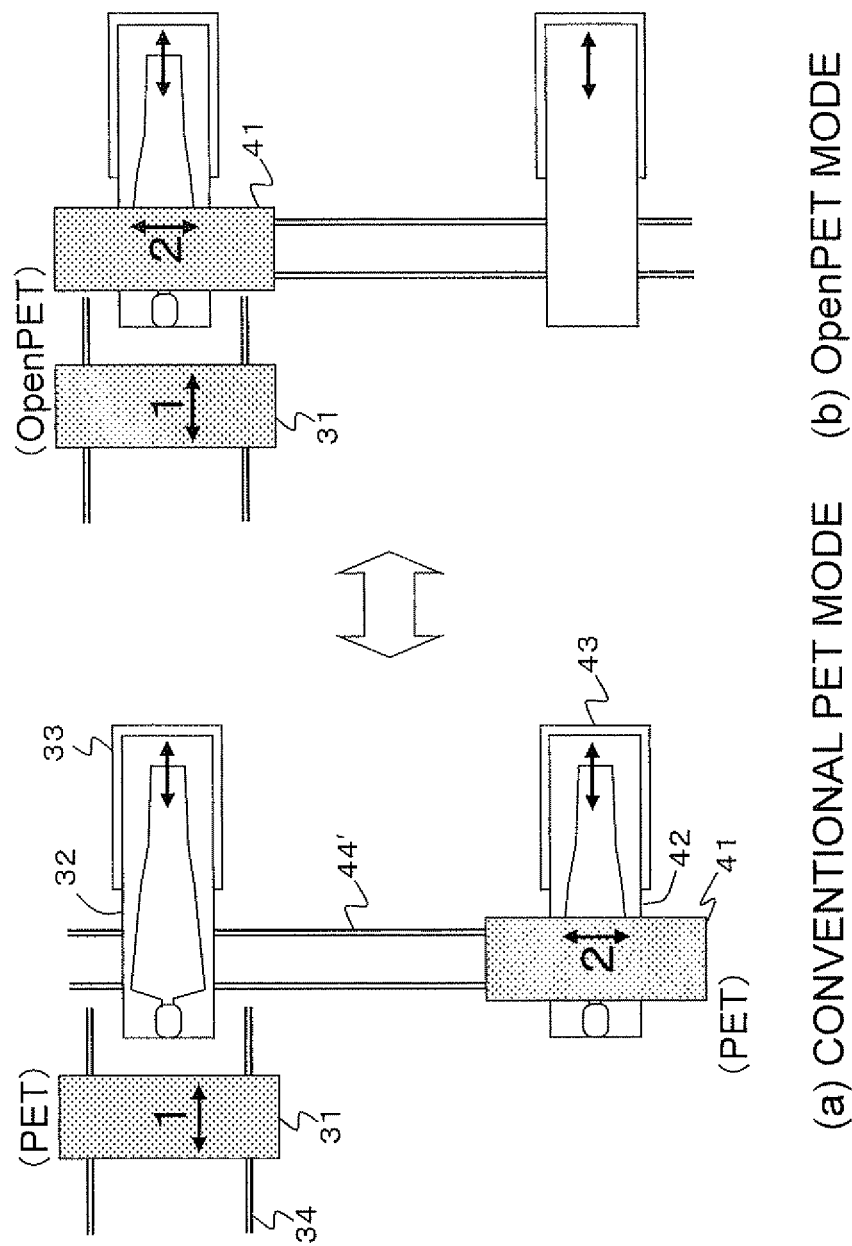
FIG. 5 is a diagram showing another configuration example of the present invention.
Figure 6:
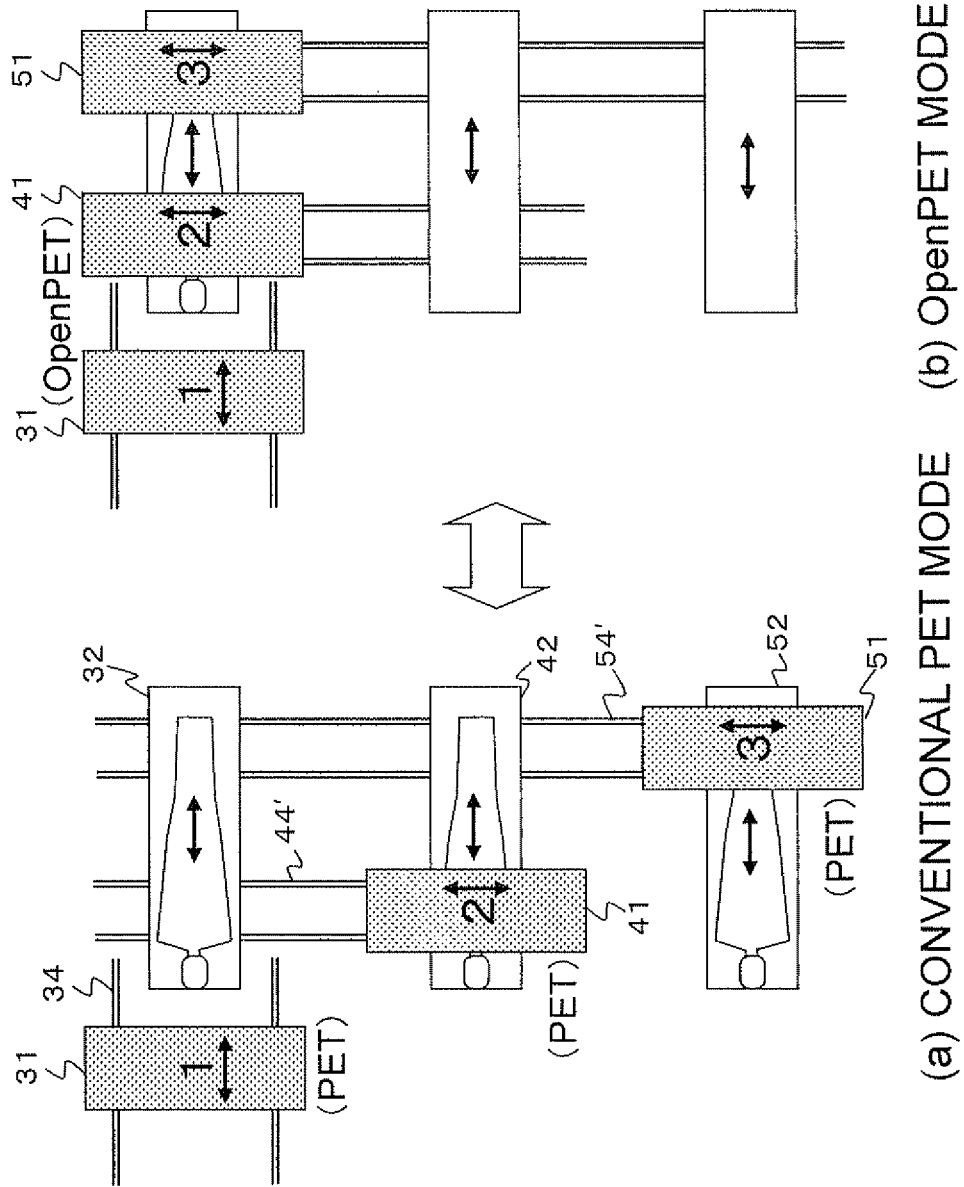
FIG. 6 is a diagram showing yet another configuration example of the present invention.
Figure 11:
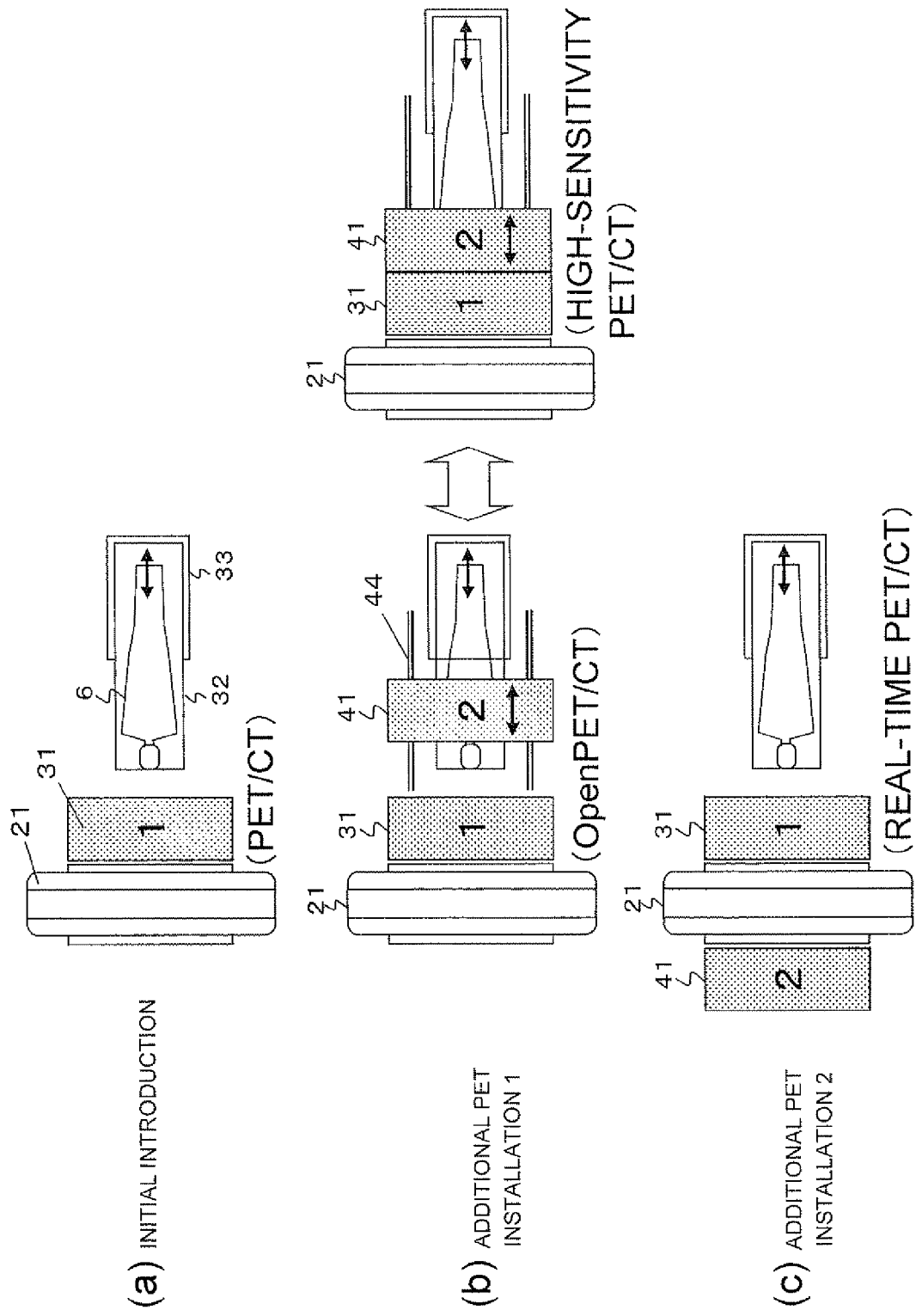
FIG. 11 is a diagram showing a third embodiment of the present invention.

FIG. 11 shows a third embodiment of the present invention, in which PET is installed more after initial introduction of a PET/CT device. As shown in FIG. 11(a), a PET device 31 and an X-ray CT device 21 are combined to share the patient bed 32. Such a configuration is prevalent for the purpose of superposing CT images having excellent morphological information over PET images to enhance the diagnostic performance of PET for the sake of compensating the drawback of PET images of less anatomical information. FIG. 11(b) shows an example where the detector ring 41 of the additional PET device is arranged on the right of the first detector ring 31 (on the opposite side from the CT device 21) to constitute an OpenPET/CT device. The second detector ring 41 may be configured to be movable on rails 44 in the direction of the body axis, thereby changing the open field of view. As shown to the right of FIG. 11(b), the detector rings 31 and 41 may be connected to constitute a high-sensitivity PET/CT. Alternatively, as shown in FIG. 11(c), the additional second detector ring 41 may be arranged so that the CT device 21 is interposed between the two detector rings 31 and 41. This can constitute a real-time PET/CT shown in FIG. 2(c).

Figure 12:
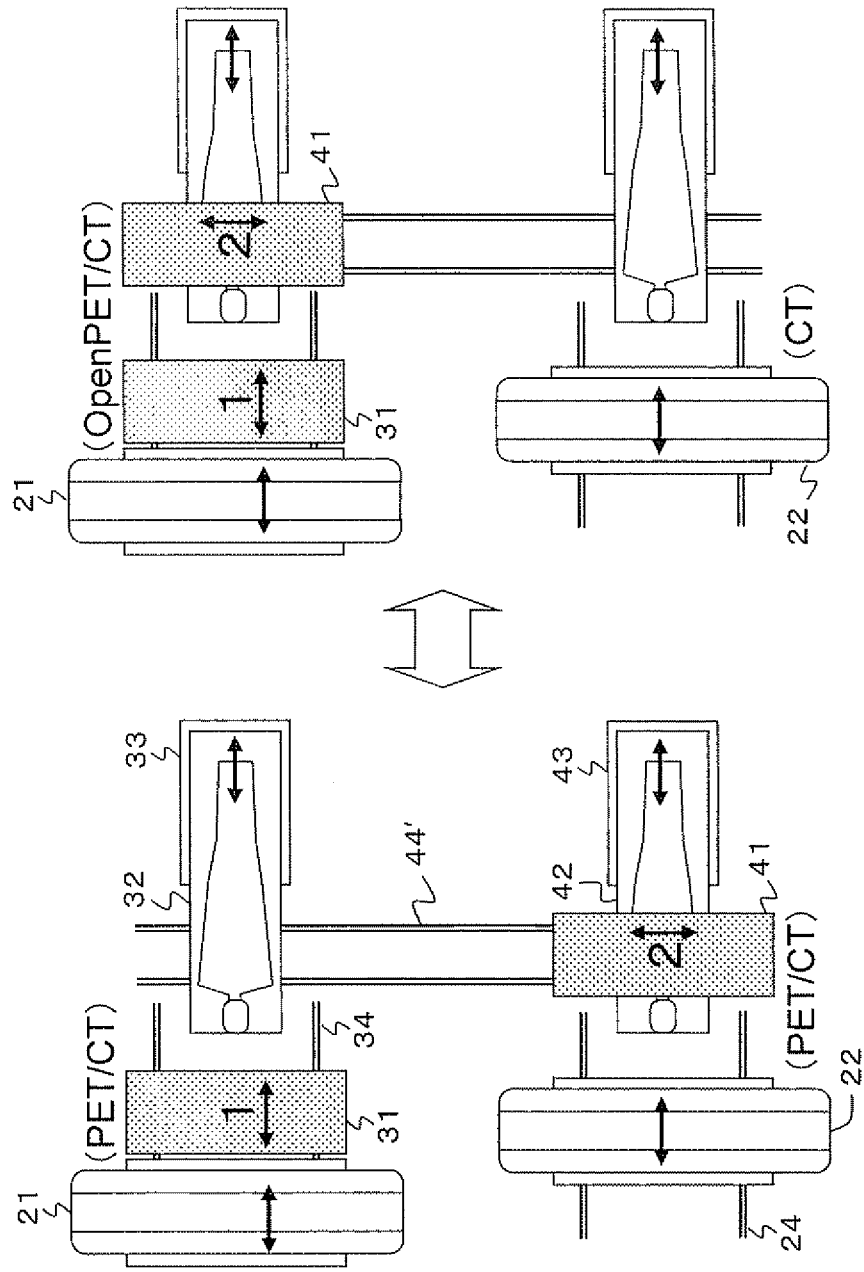
FIG. 12 is a diagram showing a fourth embodiment of the present invention.

FIG. 12 shows a fourth embodiment of the present invention, in which (a) two independently operating PET/CT devices 21+31 and 22+41 (conventional PET/CT mode) and (b) a single OpenPET/CT 21+31+41 (OpenPET/CT mode) can be switched. In (b) the OpenPET/CT mode, the remaining second CT device 22 may be used by itself. The second detector ring 41 is mounted on rails 44 that extend in a direction orthogonal to the body axis. To switch from the conventional PET/CT mode to the OpenPET/CT mode, a patient bed 42 is once withdrawn out of the second detector ring 41. The patient bed 32 is further moved to the right in the diagram. The second detector ring 41 is then moved to a position coaxial with the first detector ring 31, and the patient bed 32 is returned to the original position. The first detector ring 31 may be fixed to the floor. The first detector ring 31 may be configured to be movable on the rails 34 in the direction of the body axis so that the open field of view can be changed more freely. Since the patient bed 32 is movable in the direction of the body axis, the CT devices 21 and 22 may be fixed to the floor. The CT devices 21 and 22 may also be configured to be movable on the rails 34 and 24 in the direction of the body axis so that the distances between the CT devices 21 and 22 and the detector rings 31 and 41 of the PET devices can be changed.

Figure 13:
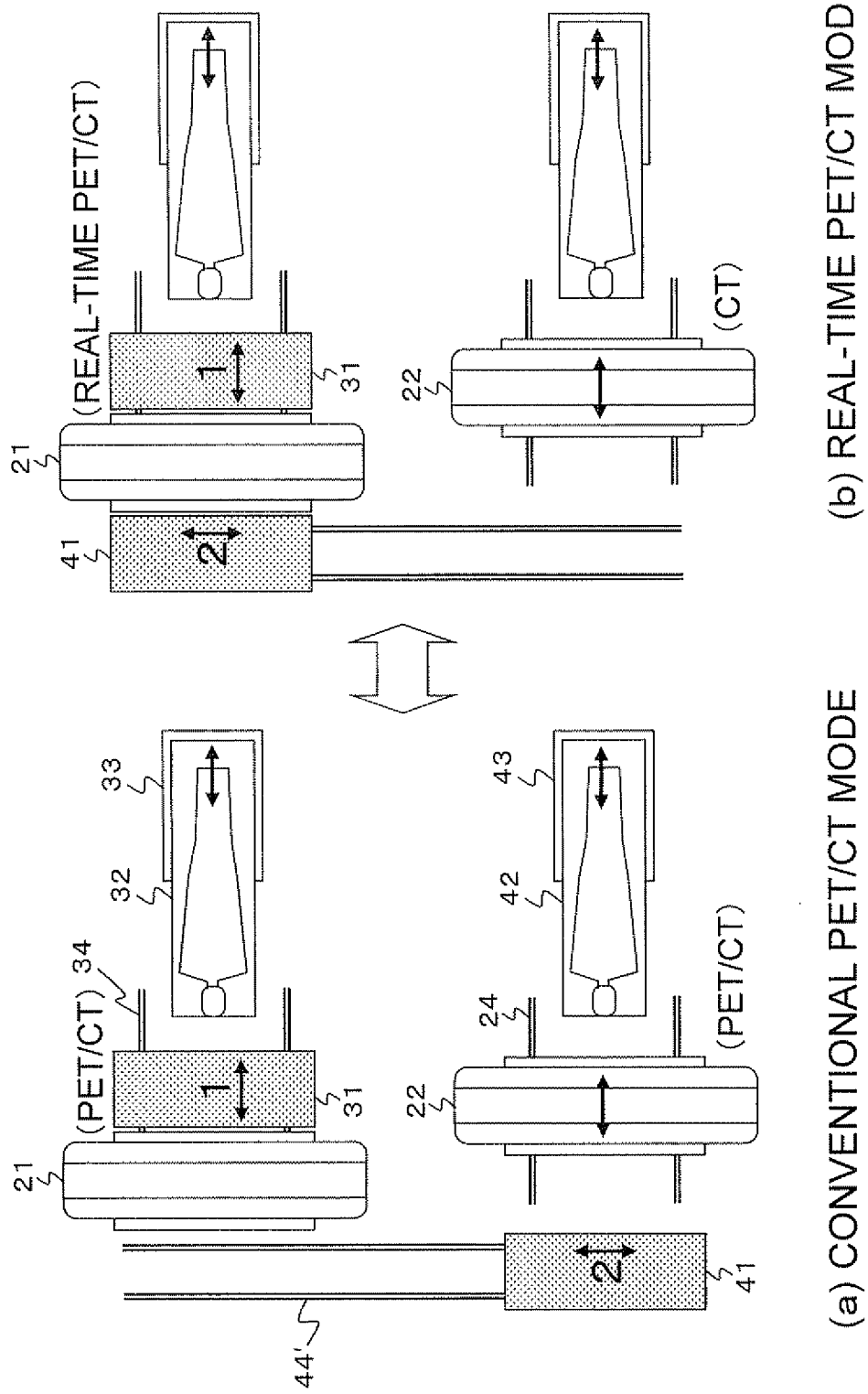
FIG. 13 is a diagram showing a fifth embodiment of the present invention.

FIG. 13 is similar to FIG. 12. FIG. 13 shows a fifth embodiment of the present invention, in which the rails 44" of the second detector ring 41 are changed in position so that the second detector ring 41 can be moved in a direction orthogonal to the body axis to interpose the first CT device 21 between the two detector rings 31 and 41. This allows switching between (a) the conventional PET/CT mode and (b) the real-time PET/CT mode. While the embodiment deals with an example where the patient beds are arranged in parallel in the same direction, the patient bed 42 and a base 43 may be in an inverted direction so that the patient enters from the PET device side (in the diagram, the left side of the detector ring 41).

Figure 14:
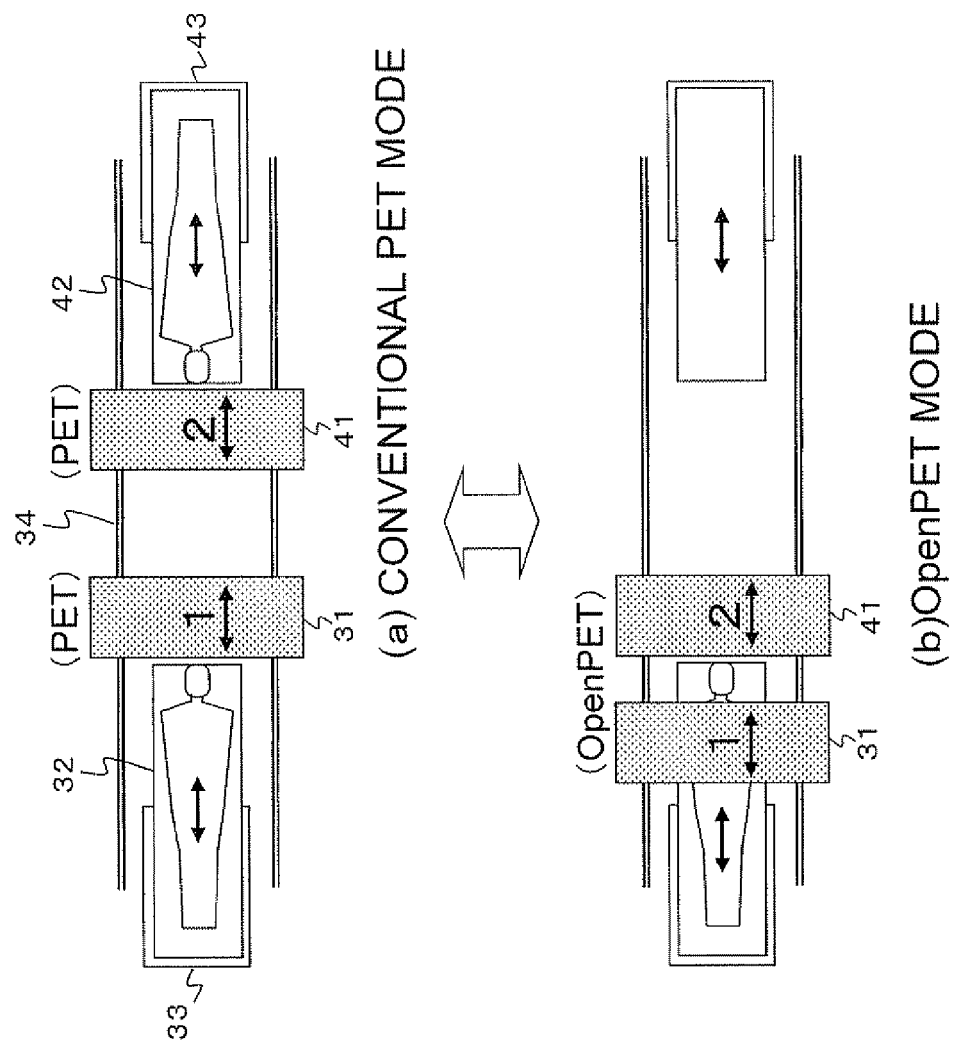
FIG. 14 is a diagram showing a sixth embodiment of the present invention.
Figure 15:
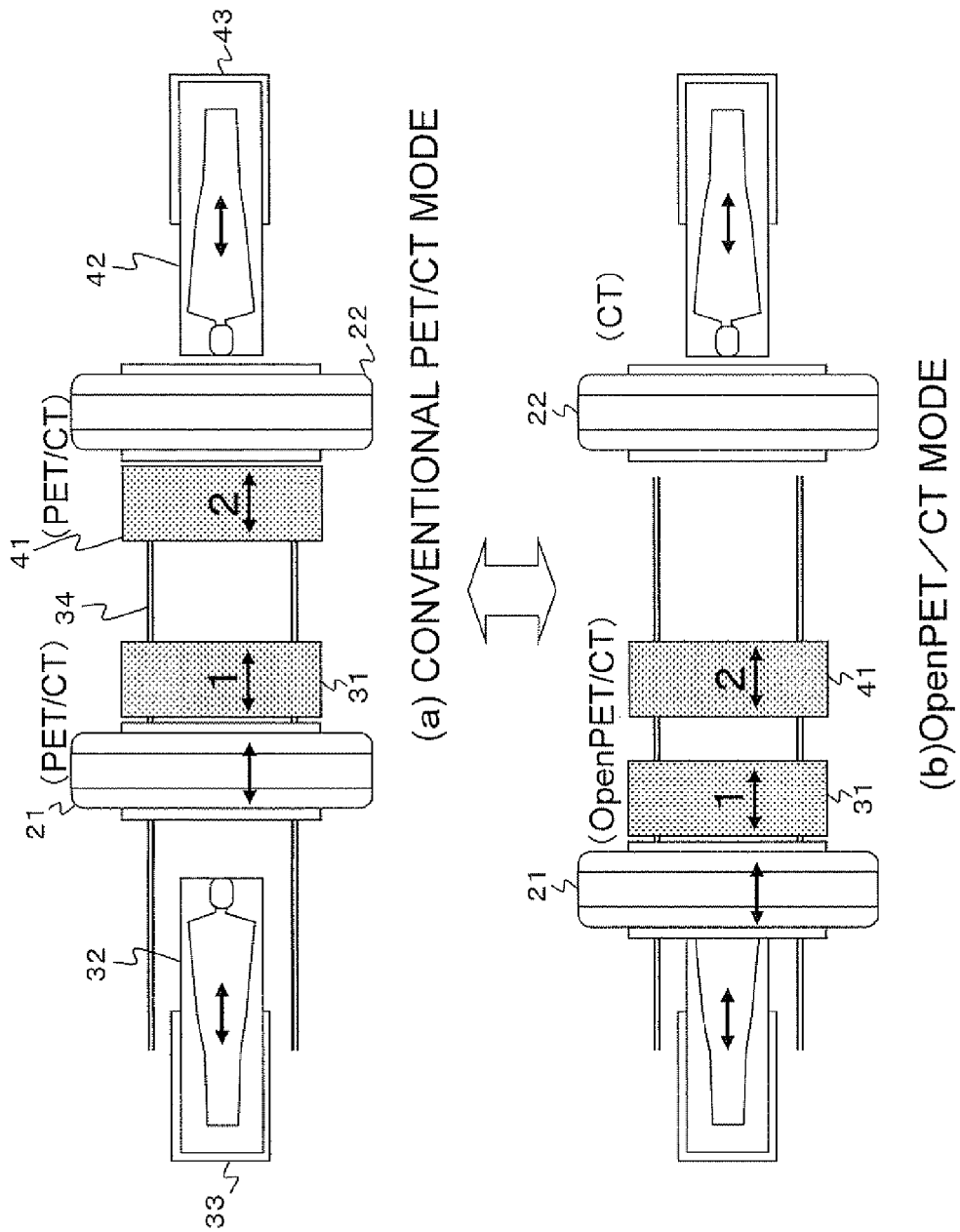
FIG. 15 is a diagram showing a seventh embodiment of the present invention.
Figure 16:
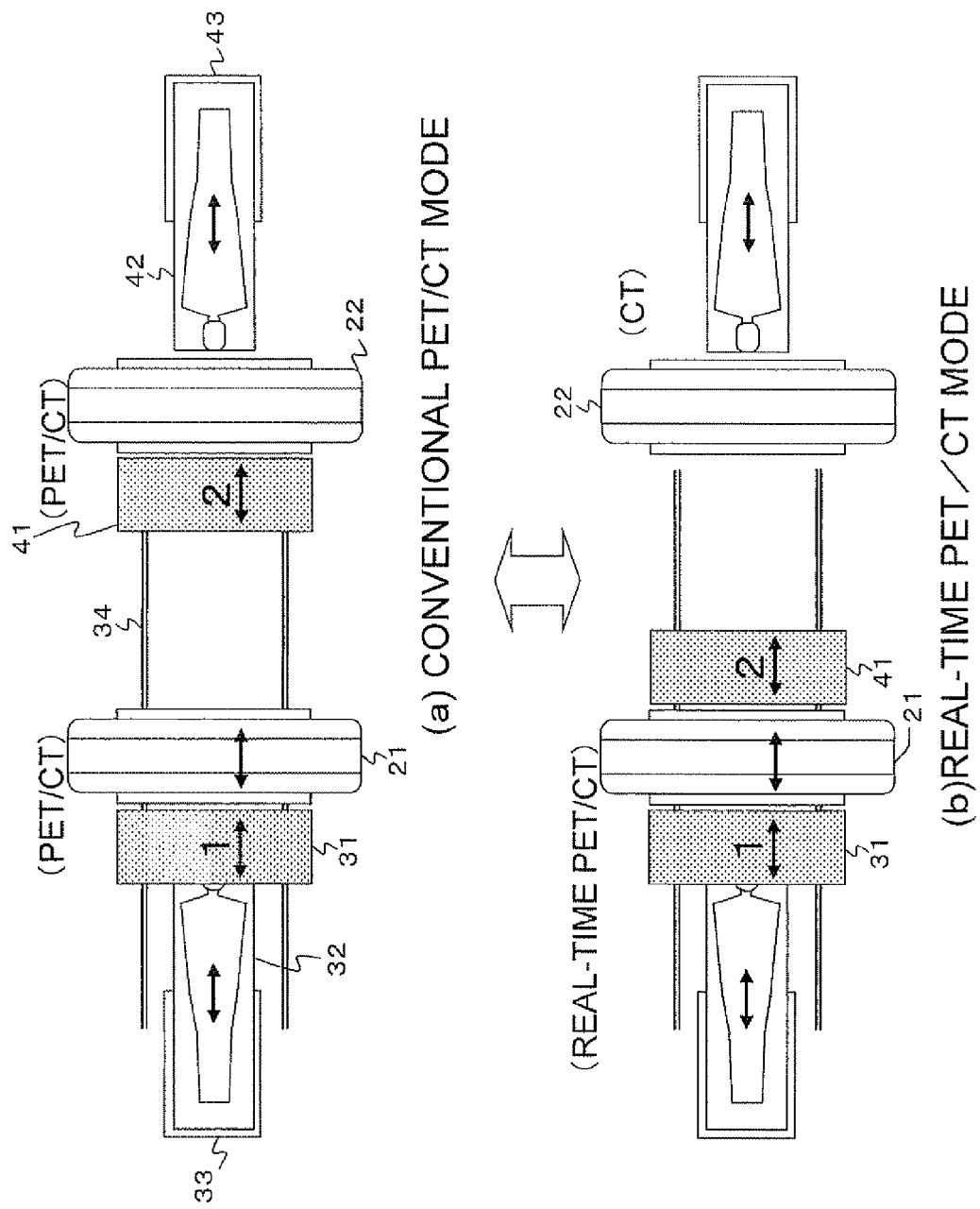
FIG. 16 is a diagram showing an eighth embodiment of the present invention.

In the foregoing examples, the two patient beds 32 and 42 are arranged in parallel. FIGS. 14 to 16 show configurations in which the two patient beds 32 and 42 are arranged on a straight line. FIG. 14 shows the configuration of a sixth embodiment of the present invention for switching (a) the conventional PET mode and (b) the OpenPET mode. FIG. 15 shows the configuration of a seventh embodiment of the present invention for switching (a) the conventional PET/CT mode and (b) the OpenPET/CT mode. FIG. 16 shows the configuration of an eighth embodiment of the present invention for switching (a) the conventional PET/CT mode and (b) the real-time PET/CT mode.

Figure 17:
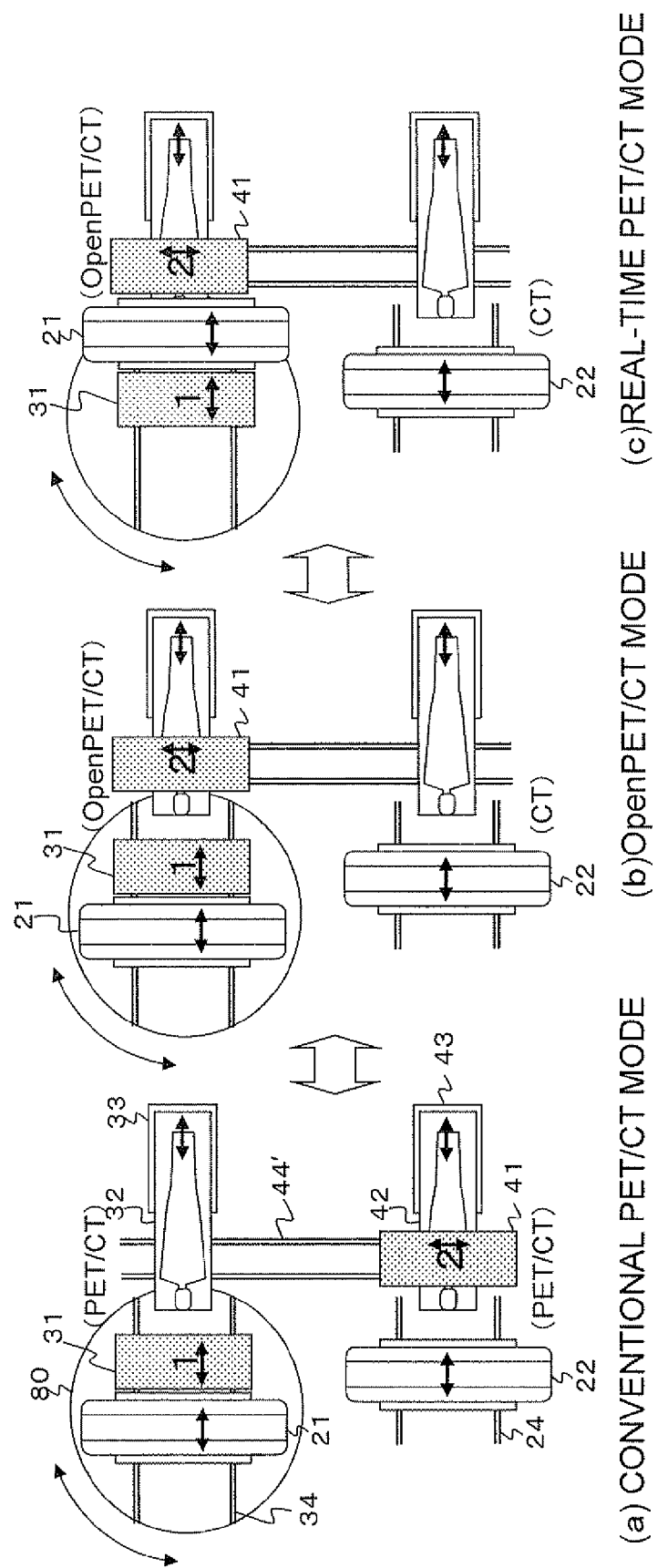
FIG. 17 is a diagram showing a ninth embodiment of the present invention.

FIGS. 12 and 15 show configuration examples that enable the OpenPET/CT mode, and FIGS. 13 and 16 show configuration examples that enable the real-time PET/CT mode. The same devices cannot be used for both the OpenPET/CT mode and the real-time PET/CT mode. A turning operation may be added to the straight movement of the devices so that, for example, the relationships of the first detector ring 31 and the first CT device 21 with respect to the second detector ring 41 can be interchanged with each other. This enables switching even between the two modes. FIG. 17 shows the configuration of a ninth embodiment of the present invention, in which the function of integrally turning the first detector ring 31 and the adjoining first CT device 21 is added to FIG. 12. In the diagram, 80 designates a turntable. The rails 34 are laid on the turntable 80.

Figure 18:
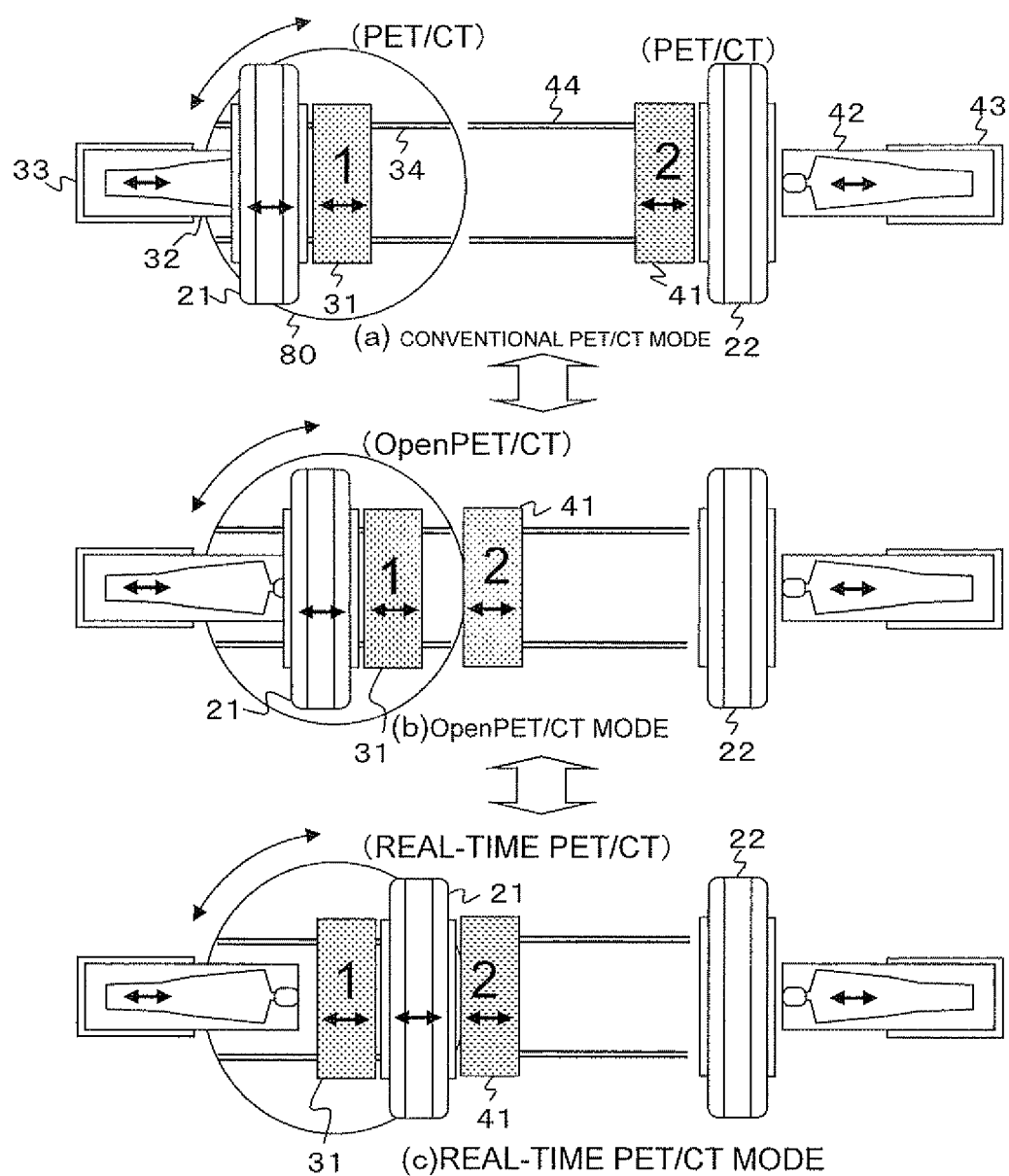
FIG. 18 is a diagram showing a tenth embodiment of the present invention.

Similarly, FIG. 18 shows the configuration of a tenth embodiment, in which the function of integrally turning the detector ring 31 and the adjoining first CT device 21 is added to FIG. 15.

In FIGS. 17 and 18, (a) the conventional PET/CT mode, (b) the OpenPET/CT mode, and (c) the real-time PET/CT mode can be switched freely.

Figure 19:
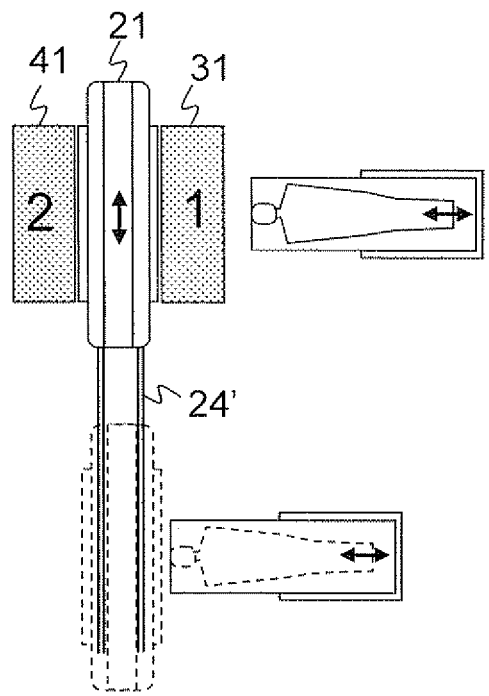
FIG. 19 is a diagram showing an eleventh embodiment of the present invention.

The foregoing examples have dealt with the cases of moving the PET device, whereas the PET device may be fixed in principle and the CT device(s) may be movable. FIG. 19 shows an eleventh embodiment which deals with an example where the detector rings 31 and 41 constituting an open PET device are fixed, and the CT device 21 which is configured to be movable on rails 24' in a direction perpendicular to the body axis is inserted into the open space. This enables switching between the real-time PET/CT mode and the OpenPET mode (the CT may also be used by itself).

Figure 20:
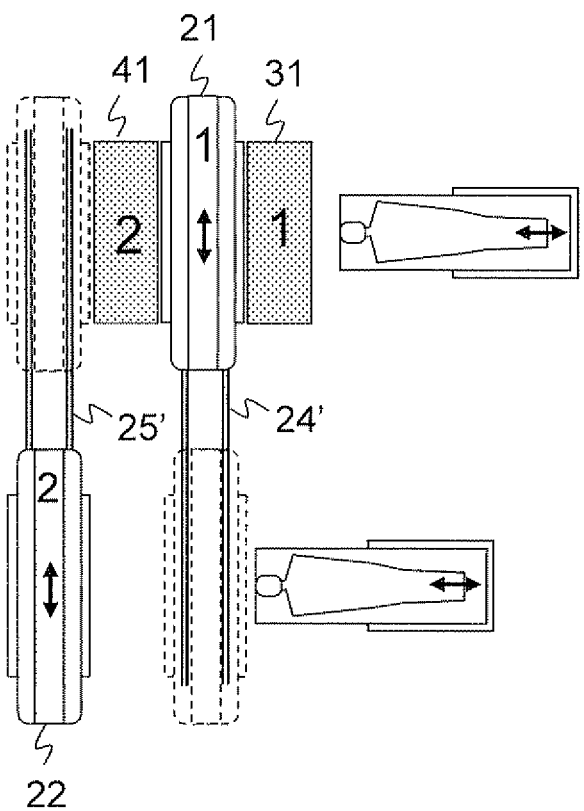
FIG. 20 is a diagram showing a twelfth embodiment of the present invention.

FIG. 20 shows a twelfth embodiment which deals with an example where a CT device 22, which is configured to be movable on rails 25' in a direction perpendicular to the body axis, is further added to the eleventh embodiment. This enables switching between the real-time PET/CT mode, the OpenPET mode, and the OpenPET/CT mode. In FIG. 20, the CT device 21 and the rails 24' may be eliminated if the real-time PET/CT mode is not needed.

FIGS. 19 and 20 have dealt with the examples where the PET device is fixed. At least either one of the detector rings 31 and 41 may be configured to be movable in the direction of the body axis so that the open field of view can be changed in size.

Incidentally, when performing a plurality of PET inspections in parallel or a PET inspection and a CT inspection in parallel, it is preferred that both the devices be shielded with movable shields so as to reduce exposure and background radioactivity (radioactivity outside the field of view).

Industrial Applicability

An open PET device, which is higher in cost than conventional PET devices, can be improved in versatility for easier introduction to facilities.

The invention claimed is:

1. A multi-purpose PET device that is an open PET device, and for use on a subject, the multi-purpose PET device comprising:
    a plurality of detector rings arranged apart from each other in a direction of a body axis of the subject;
    a physical open field of view area being formed between the rings; and
    device moving means configured to: (i) move the detector rings, or (ii) move another device into an open space in order to change a configuration of the PET device, wherein
        the moving means is configured to move at least two of the detector rings such that a first of the at least two detector rings is moved in a direction orthogonal to the body axis and a second of the at least two detector rings is moved in a direction of the body axis.

2. The multi-purpose PET device of claim 1, wherein the device moving means is configured to move the at least two detector rings simultaneously.

3. A multi-purpose PET device that is an open PET device, and for use on a subject, the multi-purpose PET device comprising:
    a plurality of detector rings arranged apart from each other in a direction of a body axis of the subject;
    a physical open field of view area being formed between the rings; and device moving means configured to: (i) move the detector rings, or (ii) move another device into an open space in order to change a configuration of the PET device, wherein another imaging device is arranged in parallel with the PET device, and the device moving means is configured to move at least two of the detector rings and the imaging device, and at least two of the detector rings of the PET device is movable close to the another imaging apparatus so as to allow use as a plurality of independent hybrid imaging devices, and the moving means is configured to move at least two of the detector rings such that a first of the at least two detector rings is moved in a direction orthogonal to the body axis and a second of the at least two detector rings is moved in a direction of the body axis.

4. The multi-purpose PET device of claim 3, wherein the device moving means is configured to move the at least two detector rings simultaneously.

5. A multi-purpose PET device that is an open PET device, and for use on a subject, the multi-purpose PET device comprising:

a plurality of detector rings arranged apart from each other in a direction of a body axis of the subject;

a physical open field of view area being formed between the rings; and device moving means configured to: (i) move the detector rings, or (ii) move another device into an open space in order to change a configuration of the PET device, wherein another imaging device is arranged in parallel with the PET device, and the device moving means is configured to move at least two of the detector rings and the imaging device, and the detector rings of the PET device with which the another imaging apparatus is arranged in parallel is rotatable, and the moving means is configured to move at least two of the detector rings such that a first of the at least two detector rings is moved in a direction orthogonal to the body axis and a second of the at least two detector rings is moved in a direction of the body axis.

6. The multi-purpose PET device of claim 5, wherein the device moving means is configured to move the at least two detector rings simultaneously.

7. A multi-purpose PET device being an open PET device comprising:

a plurality of detector rings arranged apart from each other in a direction of a body axis of a subject;

a physical open field of view area being formed between the rings;

a plurality of wheels attached to the plurality of detector rings;

a plurality of rails arranged in order to change a configuration of the PET device, the plurality of wheels being configured to move along the plurality of rails, wherein the plurality of rails is configured to move at least two of the detector rings such that a first of the at least two detector rings is moved in a direction orthogonal to the body axis and a second of the at least two detector rings is moved in a direction of the body axis.

8. The multi-purpose PET device of claim 7, wherein the at least two detector rings move simultaneously.

9. A multi-purpose PET device being an open PET device comprising:

a plurality of detector rings arranged apart from each other in a direction of a body axis of a subject;

a physical open field of view area being formed between the rings;

a plurality of wheels attached to the plurality of detector rings;

a plurality of rails arranged in order to change a configuration of the PET device, the plurality of wheels being configured to move along the plurality of rails, wherein another imaging device is arranged in parallel with the PET device, and the plurality of rails is configured to move at least two of the detector rings and the imaging device, and at least two of the detector rings of the PET device is movable close to the another imaging apparatus so as to allow use as a plurality of independent hybrid imaging devices, and the plurality of rails is configured to move at least two of the detector rings such that a first of the at least two detector rings is moved in a direction orthogonal to the body axis and a second of the at least two detector rings is moved in a direction of the body axis.

10. The multi-purpose PET device of claim 9, wherein the at least two detector rings move simultaneously.

11. A multi-purpose PET device being an open PET device comprising:

a plurality of detector rings arranged apart from each other in a direction of a body axis of a subject;

a physical open field of view area being formed between the rings;

a plurality of wheels attached to the plurality of detector rings;

a plurality of rails arranged in order to change a configuration of the PET device, the plurality of wheels being configured to move along the plurality of rails, wherein another imaging device is arranged in parallel with the PET device, and the plurality of rails is configured to move at least two of the detector rings and the imaging device, and the detector rings of the PET device with which the another imaging apparatus is arranged in parallel is rotatable, and the plurality of rails is configured to move at least two of the detector rings such that a first of the at least two detector rings is moved in a direction orthogonal to the body axis and a second of the at least two detector rings is moved in a direction of the body axis.

12. The multi-purpose PET device of claim 11, wherein the at least two detector rings move simultaneously.

* * * * *